(12) United States Patent
Ohno

(10) Patent No.: US 10,993,637 B2
(45) Date of Patent: May 4, 2021

(54) OPERATING APPARATUS FOR MEDICAL APPARATUS

(71) Applicant: SONY OLYMPUS MEDICAL SOLUTIONS INC., Hachioji (JP)

(72) Inventor: Naoyuki Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 995 days.

(21) Appl. No.: 14/893,344

(22) PCT Filed: Jan. 14, 2015

(86) PCT No.: PCT/JP2015/050800
§ 371 (c)(1),
(2) Date: Nov. 23, 2015

(87) PCT Pub. No.: WO2015/151543
PCT Pub. Date: Oct. 8, 2015

(65) Prior Publication Data
US 2016/0128607 A1    May 12, 2016

(30) Foreign Application Priority Data
Mar. 31, 2014  (JP) .............................. JP2014-072113

(51) Int. Cl.
*A61B 5/06* (2006.01)
*G01D 5/245* (2006.01)
(Continued)

(52) U.S. Cl.
CPC .......... *A61B 5/062* (2013.01); *A61B 1/00006* (2013.01); *A61B 1/00009* (2013.01);
(Continued)

(58) Field of Classification Search
CPC ... A61B 1/04; A61B 1/00158; A61B 1/00188; A61B 1/00066; A61B 1/00142; A61B 1/121; A61B 1/042; G01D 5/145
See application file for complete search history.

(56) References Cited

U.S. PATENT DOCUMENTS 7,741,839 B2 *  6/2010  Jarrard ................. H01F 7/0294
                                                       324/207.2
2005/0127762 A1 *  6/2005  Miyashita ............. G01D 5/145
                                                       318/400.38
(Continued)

FOREIGN PATENT DOCUMENTS

CN     102066879 A    5/2011
CN     102207778 A    10/2011
(Continued)

OTHER PUBLICATIONS

Engineering Design Handbook—Environmental Series, Part Five—Glossary of Environmental Terms: (AMCP 706-119)—hoarfrost (commonly called frost). U.S. Army Materiel Command. Retrieved from https://app.knovel.com/hotlink/pdf/id:kt008MS8l1/engineering-design-handbook-25/hoarfrost-commonly-called (Year: 1975).*
(Continued)

*Primary Examiner* — Alexandra L Newton
(74) *Attorney, Agent, or Firm* — Xsensus LLP

(57) ABSTRACT

There is provided an operating apparatus for a medical apparatus, the operating apparatus including a ring-shaped magnet magnetically polarized in a circumferential direction or a radial direction and configured to rotate along with rotating operation by a user, and a sensor unit configured to detect a magnetic field and to output a signal depending on the detected magnetic field. The sensor unit outputs two-phase signals having different phases.

23 Claims, 10 Drawing Sheets

(51) Int. Cl.
   *A61B 1/00*     (2006.01)
   *G06F 3/0362*   (2013.01)
   *A61B 1/045*    (2006.01)
   *A61B 5/05*     (2021.01)
   *A61B 5/00*     (2006.01)
   *A61B 17/00*    (2006.01)

(52) U.S. Cl.
   CPC ...... *A61B 1/00039* (2013.01); *A61B 1/00066* (2013.01); *A61B 1/00105* (2013.01); *A61B 1/00124* (2013.01); *A61B 1/00158* (2013.01); *A61B 1/00188* (2013.01); *A61B 1/045* (2013.01); *A61B 5/05* (2013.01); *A61B 5/7475* (2013.01); *A61B 17/00234* (2013.01); *G01D 5/2451* (2013.01); *G06F 3/0362* (2013.01); *A61B 2562/0223* (2013.01)

(56) References Cited

U.S. PATENT DOCUMENTS

| | | | | |
|---|---|---|---|---|
| 2005/0267329 | A1* | 12/2005 | Konstorum | A61B 1/00039 600/112 |
| 2010/0125166 | A1* | 5/2010 | Henzler | A61B 1/00177 600/109 |
| 2011/0156505 | A1 | 6/2011 | Miyashita et al. | |
| 2011/0241657 | A1 | 10/2011 | Nishiono et al. | |
| 2012/0238808 | A1* | 9/2012 | Teichtmann | A61B 1/00025 600/109 |
| 2013/0268234 | A1 | 10/2013 | Janisch | |
| 2014/0275780 | A1* | 9/2014 | Feingold | A61B 1/045 600/109 |
| 2014/0285644 | A1* | 9/2014 | Richardson | A61B 1/00009 348/68 |

FOREIGN PATENT DOCUMENTS

| | | |
|---|---|---|
| DE | 10 2008 033 365 A1 | 1/2010 |
| JP | 11-175248 | 7/1999 |
| JP | 11-175248 A | 7/1999 |
| JP | 2002-315753 | 10/2002 |
| JP | 2002-315753 A | 10/2002 |
| JP | 2006-25913 | 2/2006 |
| JP | 2009-503715 | 1/2009 |
| JP | 2010-191811 A | 9/2010 |
| JP | 2011-210078 | 10/2011 |
| JP | 2011-210078 A | 10/2011 |
| WO | WO 2004/066138 A1 | 8/2004 |

OTHER PUBLICATIONS

Combined Office Action and Search Report dated Aug. 28, 2017 in Chinese Patent Application No. 201580000890.9 (with English language translation).

Combined Office Action and Search Report dated Mar. 14, 2018 in Chinese Patent Application No. 201580000890.9 (with English language translation), 15 pages.

Extended European Search Report dated Jan. 19, 2017 in Patent Application No. 15774356.8.

International Search Report dated Apr. 14, 2015 in PCT/JP2015/050800 (with English language translation).

Japanese Office Action dated Dec. 11, 2018 in Japanese Patent Application No. 2015-549895, 4 pages.

Office Action dated Apr. 9, 2019, in Japan Patent Application No. 2015-549895, 5 pgs.

* cited by examiner

UNIT: mm

OPERATING APPARATUS FOR MEDICAL APPARATUS

TECHNICAL FIELD

The present disclosure relates to an operating apparatus for a medical apparatus.

BACKGROUND ART

Examples of an operating apparatus for a medical apparatus include an operating apparatus using magnetism for manually controlling and adjusting a medical imaging apparatus. Such an operating apparatus using magnetism has already been developed. Examples of technology related to an operating apparatus using magnetism include those described in Patent Literatures 1 and 2 below.

CITATION LIST

Patent Literature

Patent Literature 1: JP 2010-191811A
Patent Literature 2: WO 2004/066138

SUMMARY OF INVENTION

Technical Problem

In an existing medical operating apparatus using magnetism (herein after, referred to as "existing operating apparatus") uses a method of "moving an internal member using magnetic attraction," or "causing a magnetic sensor to sense whether or not it is included in a magnetic field," for example. However, even by using the existing operating apparatus, it has been still difficult to realize precise control and adjustment according to user operation. Accordingly, there is demanded an operating apparatus capable of causing processing according to user operation to be performed.

The present disclosure proposes a novel and improved operating apparatus for a medical apparatus, the operating apparatus being capable of causing processing according to user operation to be performed.

Solution to Problem

According to the present disclosure, there is provided an operating apparatus for a medical apparatus, the operating apparatus including: a ring-shaped magnet magnetically polarized in a circumferential direction or a radial direction and configured to rotate along with rotating operation by a user; and a sensor unit configured to detect a magnetic field and to output a signal depending on the detected magnetic field. The sensor unit outputs two-phase signals having different phases.

Advantageous Effect of Invention

The present disclosure enables causing processing according to user operation to be performed.

Note that the effect described above is not necessarily limited, and along with or instead of the effect, any effect that is desired to be introduced in the present specification or other effects that can be expected from the present specification may be exhibited.

DESCRIPTION OF EMBODIMENT

Hereinafter, a preferred embodiment of the present disclosure will be described in detail with reference to the appended drawings. Note that, in this specification and the drawings, elements that have substantially the same function and structure are denoted with the same reference signs, and repeated explanation is omitted.

Hereinafter, description will be given in the following order.

1. Operating apparatus according to the present embodiment
2. Program according to the present embodiment

Operating Apparatus According to the Present Embodiment

An operating apparatus according to the present embodiment causes processing according to user operation to be performed by outputting two-phase signals having different phases and depending on rotating operation by the user.

Examples of a target that the operating apparatus according to the present embodiment causes to perform processing according to user operation on the basis of two-phase signals include a processing unit (described later) included in the operating apparatus according to the present embodiment, and an external processing apparatus functioning similarly to the processing unit. Description will be given later of an example of the two-phase signal based processing performed by the processing unit (described later) according to the present embodiment or the like.

Hereinafter, description will be given of a configuration and processing of the operating apparatus according to the present embodiment by using, as an example, the case where the operating apparatus according to the present embodiment is applied to a medical endoscopic apparatus. Note that a medical apparatus to which the operating apparatus according to the present embodiment is applied is not limited to an endoscopic apparatus. The operating apparatus according to the present embodiment can be applied to any medical apparatus capable of being caused to perform processing according to user operation by a mechanism to be described later.

Figure 1:
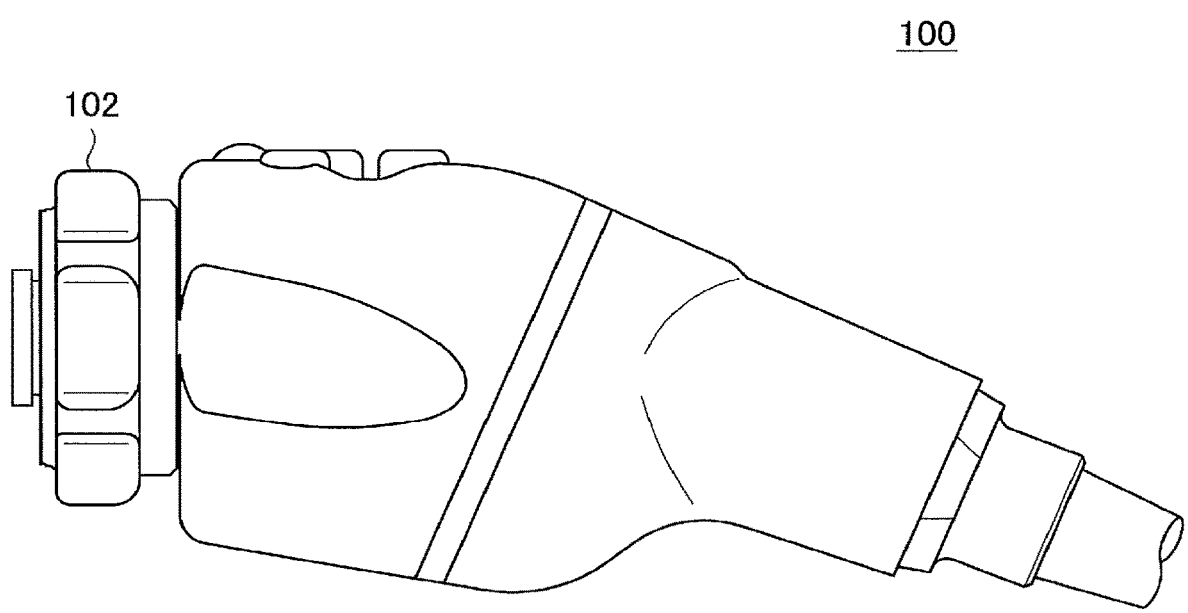
FIG. 1 is an illustration for illustrating an example of an operating apparatus according to an embodiment of the present disclosure.

FIG. 1 is an illustration for illustrating an example of the operating apparatus 100 according to the present embodiment. The operating apparatus 100 shown in FIG. 1 is an operating apparatus applied to a medical endoscopic apparatus (operating apparatus used for controlling and adjusting a medical endoscopic apparatus).

The operating apparatus 100 includes an operating ring 102 which is rotationally operable by a user, for example. The operating ring 102 freely rotates clockwise or counterclockwise. The user of the operating apparatus 100 can perform desirable clockwise or counterclockwise rotating operation by operating the operating ring 102. When the user rotationally operates the operating ring 102, the operating apparatus 100 outputs two-phase signals corresponding to this rotating operation of the operating ring 102, and thereby causes processing according to the user operation to be performed.

Examples of processing depending on rotating operation of the operating ring 102 include focus-related (focusing-related) processing depending on a rotational direction, as described below. When the processing depending on rotating operation is focus-related processing depending on a rotational direction, the operating ring 102 functions as a so-called focus ring.

When the rotational direction is clockwise (viewed from the surgeon's side (endoscopic apparatus) to the patient's side), the focused point moves forward.

When the rotational direction is clockwise (viewed from the surgeon's side (endoscopic apparatus) to the patient's side), the focused point moves backward.

When the rotational speed of the rotationally operated operating ring 102 is detected to be a predetermined value or more, currently performed processing such as focus-related processing may be cancelled, or preset processing may be performed.

Obviously, examples of the processing depending on rotating operation of the operating ring 102 are not limited to those described above.

Though the operating ring 102 is freely rotatable as described above, the upper and lower limits corresponding to a drive range of the operating ring 102 may be put on the processing depending on rotating operation. Putting the upper and lower limits corresponding to the drive range will, for example, realize that, when the upper or lower limit corresponding to the drive range is exceeded, the operating ring 102 rotates but, in the focus-related processing (example of the processing depending on rotating operation), the focused point does not move from the position corresponding to the upper or lower limit, for example.

When the operating ring 102 is rotationally operated while processing or control different from the processing depending on rotating operation is being performed, the processing depending on rotating operation may be preferentially performed over this different processing or control. For example, when the user rotationally operates the operating ring 102 while auto focus (AF) control is being performed, the focus control is switched from AF control to manual focus (MF) control, and the focus-related processing depending on rotational direction of the operating ring 102 (example of the processing depending on rotating operation) is performed. Preferentially performing the rotating operation of the operating ring 102 over other different processing or control enables the user to manually perform fine focusing by operating the operating ring 102 even during AF control, for example.

Here, assume again the case where the processing depending on rotating operation is focus-related processing depending on a rotational direction. In this case, when the user instructs reset with reset operation or the like while performing focusing using the operating ring 102 (in so-called MF mode), the focus-related processing is restarted from, for example, the focused point adjusted with the last operation. On the other hand, when the user instructs reset with reset operation and the like during automatic focusing (in so-called AF mode), the focused point is readjusted from, for example, the focused point adjusted with AF control. Obviously, the focused point from which the focused point adjustment is restarted in response to a reset instruction is not limited to the examples described above.

[1] Configuration Related to Two-Phase Signal Output According to the Present Embodiment

[1-1] Exemplary Configuration Capable of Detecting Rotating Operation by a User

Before describing a configuration related to two-phase signal output according to the present embodiment, an exemplary configuration capable of detecting rotating operation by a user will be described.

Figure 2:
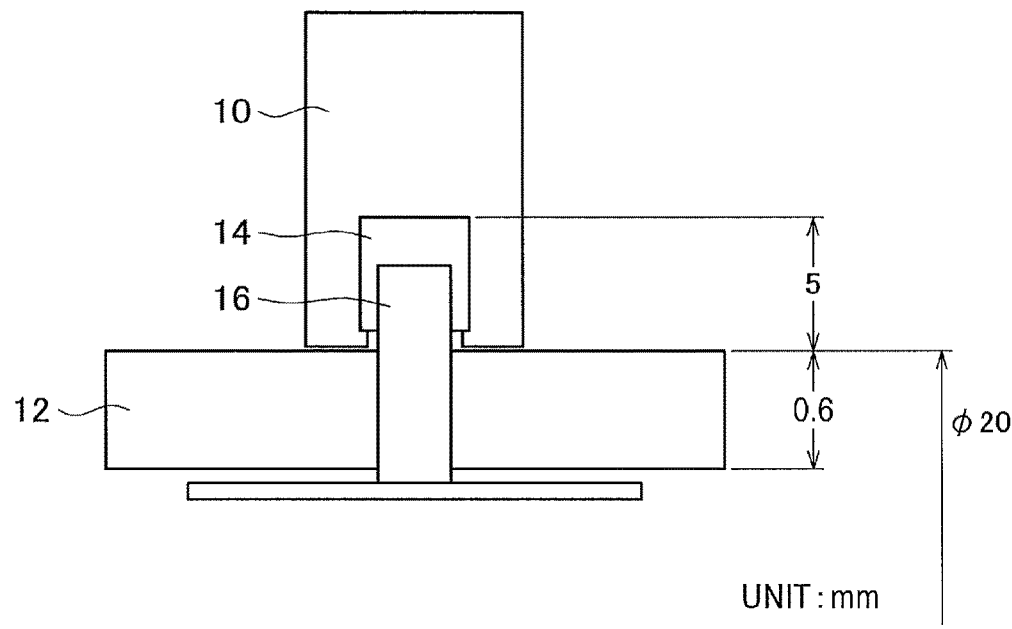
FIG. 2 is an illustration for illustrating an example of an operating apparatus having a configuration capable of detecting rotating operation by a user.

FIG. 2 is an illustration for illustrating an example of an operating apparatus having a configuration capable of detecting rotating operation by a user, which configuration is based on a photo interrupter (PI)/photo reflector (PR) method.

The operating apparatus having a configuration based on the PI/PR method includes an operating ring 10, an exterior part 12, an interdigital member 14 and a PI sensor (PR sensor) 16, for example.

The operating apparatus having a configuration based on the PI/PR method uses, as a signal depending on rotating operation by a user, a pulse signal corresponding to the interdigital shape detected by the PI sensor (PR sensor) 16 depending on the rotation of the operating ring 10.

A medical apparatus such as a medical endoscopic apparatus is sterilized after use by autoclaving (high-temperature and high-pressure steam sterilization) in an environment at approximately 140[° C.]. Accordingly, a medical apparatus is demanded to be resistant to autoclaving. In order to make a medical endoscopic apparatus resistant to autoclaving, components such as a lens unit (described later) are placed in an airtight and waterproof sealed structure, for example. Placing the components such as the lens unit (described later) in the sealed structure prevents steam for autoclaving from flowing therein, and thus prevents the components such as the lens unit (described later) from being damaged by autoclaving.

However, when the PI/PR method is employed, the exterior part 12 has to have a hole, as shown in FIG. 2. Accordingly, the configuration using the PI/PR method is not expected to have the aforementioned resistance to autoclaving. Therefore, it is not preferable to apply, to a medical apparatus, the operating apparatus having a configuration based on the PI/PR method.

In addition, the configuration using the PI/PR method have to be provided with the interdigital member 14, as shown in FIG. 2, thus being disadvantageous in miniaturization.

Figure 3:
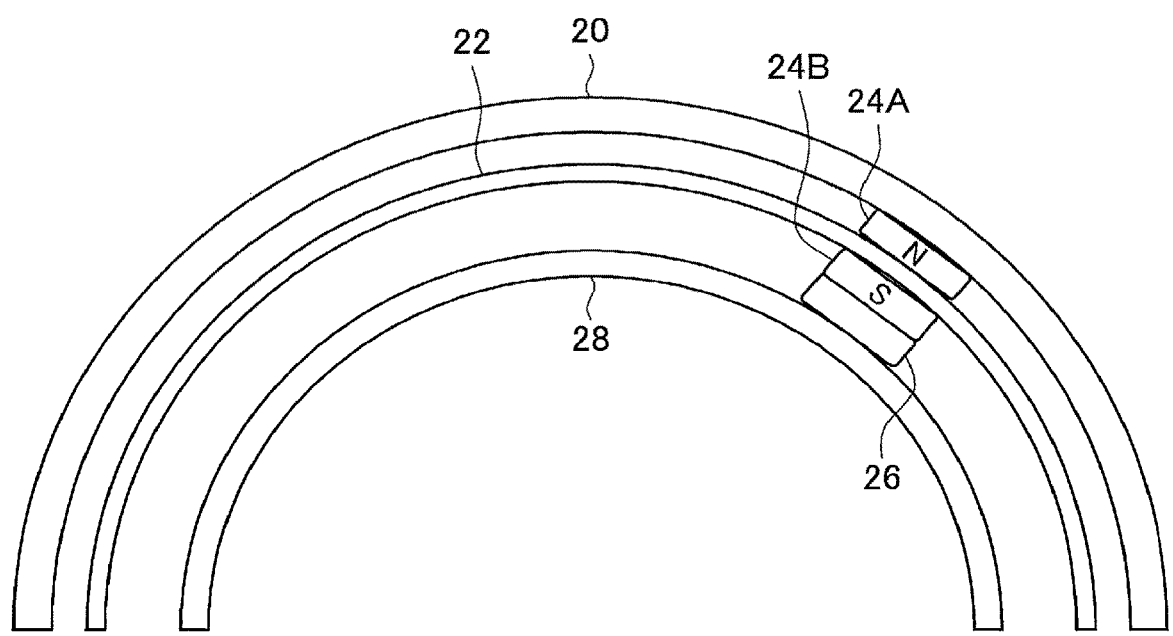
FIG. 3 is an illustration for illustrating another example of an operating apparatus having a configuration capable of detecting rotating operation by a user.

FIG. 3 is an illustration for illustrating another example of an operating apparatus having a configuration capable of detecting rotating operation by a user, which configuration is based on a variable resistance method.

The operating apparatus having a configuration based on the variable resistance method includes an operating ring 20, an exterior part 22, an N-pole magnet 24A, an S-pole magnet 24B, a wiper 26 and a variable resistor 28, for example. The exterior part 22, which does not shield a magnetic field, separates the N-pole magnet 24A from the S-pole magnet 24B.

In the operating apparatus having a configuration based on the variable resistance method, the N-pole magnet 24A moves along with the rotation of the operating ring 20, and magnetic attraction thereof moves the S-pole magnet 24B, so that the wiper 26 moves together with the S-pole magnet 24B. The resistance value of the variable resistor 28 changes depending on the position of the wiper 26, and the operating apparatus having a configuration based on the variable resistance method uses, as a signal depending on rotating operation by a user, a signal depending on the position of the wiper 26, thus on the resistance value of the variable resistor 28.

When the variable resistance method is employed, the variable resistor having a finite length have to have satisfactory fine resolution related to operation detection. However, when the variable resistance method is employed, even if the variable resistor is well-devised in mechanical designing, it is difficult to make the resolution related to operation detection fine enough to be applicable to focusing or the like.

Figure 4:
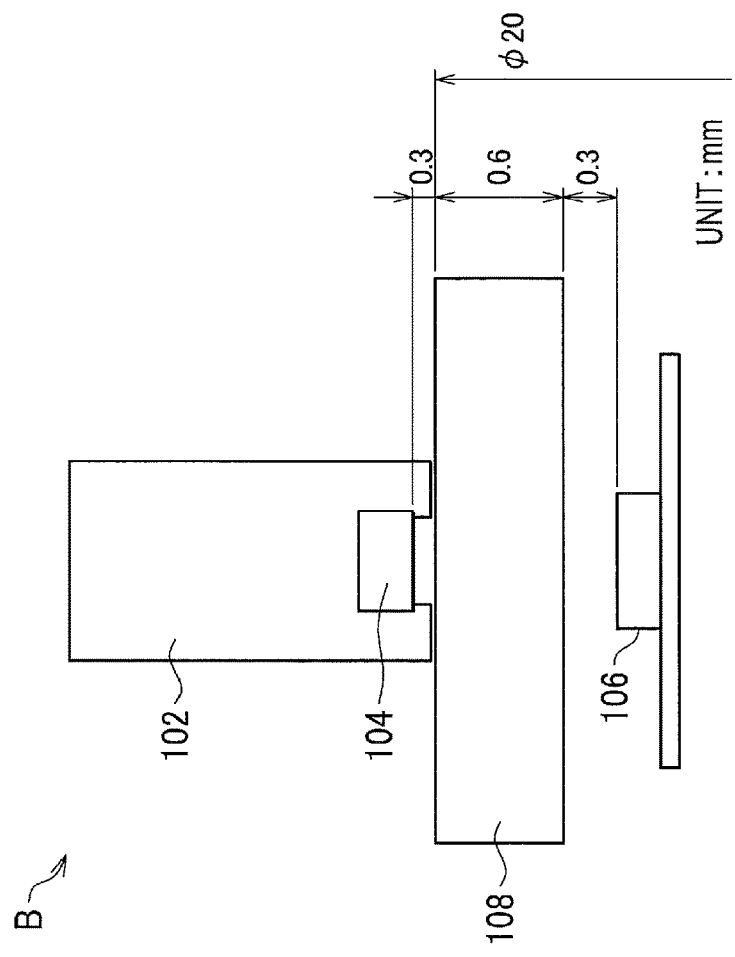
FIG. 4 is an illustration showing an exemplary configuration related to two-phase signal output in the operating apparatus according to the embodiment.
Figure 4:
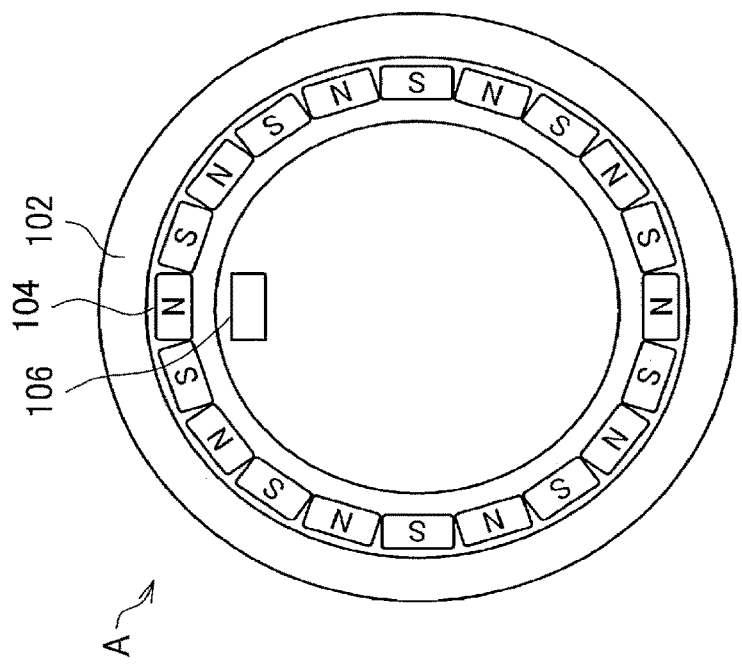

[1-2] Configuration Related to Two-Phase Signal Output According to the Present Embodiment FIG. 4 is an illustration showing an exemplary configuration related to two-phase signal output in the operating apparatus 100 according to the present embodiment. The part A of FIG. 4 schematically shows a cross section in the depth direction in FIG. 1 of, for example, a portion, provided with the operating ring 102, of the operating apparatus 100 shown in FIG. 1. The part B of FIG. 4 schematically and partially shows a cross section in the vertical direction in FIG. 1 of, for example, a portion, provided with the operating ring 102, of the operating apparatus 100 shown in FIG. 1.

The operating apparatus 100 includes a ring-shaped magnet 104 and a sensor unit 106, for example.

The ring-shaped magnet 104 includes N-pole magnets and S-pole magnets alternately arranged in the ring circumferential direction, and rotates along with rotating operation by a user. In other words, the ring-shaped magnet 104 is a ring-shaped magnet magnetized with multiple poles. In the example of FIG. 4, the ring-shaped magnet 104 moves together with the operating ring 102 when the user rotationally operates the operating ring 102.

The sensor unit 106 detects magnetic fields, and outputs signals depending on the detected magnetic fields. Specifically, the sensor unit 106 outputs two-phase signals having different phases. The sensor unit 106 is placed so as not to contact the ring-shaped magnet 104 as shown, for example, in FIG. 4 and is immovable by magnetic force of the ring-shaped magnet 104.

More specifically, the sensor unit 106 may include a sensor to output two-phase signals, for example. Alternatively, the sensor unit 106 may include two sensors: a sensor to output one signal (hereinafter referred to as "A-phase signal" or sometimes simply as "A phase") of the two-phase signals; and a sensor to output the other signal (hereinafter referred to as "B-phase signal" or sometimes simply as "B phase") of the two-phase signals.

In the following description, there will be used, as an example, the case where the sensor unit 106 includes two sensors of two sensors: a sensor to output an A-phase signal and a sensor to output a B-phase signal. Note that the sensor unit 106 being a sensor to output two-phase signals is equivalent to the sensor having both the function of the sensor to output an A-phase signal and the function of the sensor to output a B-phase signal. Thus, even when the sensor unit 106 is a sensor to output two-phase signals, the two-phase signals outputted by the sensor unit 106 is similar to those described in the following example.

Examples of the sensors included in the sensor unit 106 include a hall sensor. However, each sensor included in the sensor unit 106 may be a sensor using any method that is capable of detecting magnetic fields generated by the ring-shaped magnet 104 without contacting the ring-shaped magnet 104.

The sensor unit 106 includes a comparator (not shown), for example, and converts analog signals depending on the detected magnetic fields outputted by the hall sensors into signals each switching between high level and low level, that is, signals (digital signal) with signal levels each corresponding to the detected magnetic field, and outputs the signals with the signal levels corresponding to the detected magnetic fields. When the ring-shaped magnet 104 includes N-pole magnets and S-pole magnets alternately arranged in the circumferential direction thereof as shown in A of FIG. 4, the sensor unit 106 outputs signals (digital signals) with signal levels each corresponding to either of the magnetic poles. The sensor unit 106 may further include a latch circuit (not shown), for example.

Note that the configuration of the sensor unit 106 according to the present embodiment is not limited to a configuration including a comparator (not shown) or the like. For example, the sensor unit 106 according to the present embodiment may have a configuration not including a comparator (not shown) or the like to output analog signals depending on the detected magnetic fields outputted by hall sensors or the like. When the sensor unit 106 according to the present embodiment does not include a comparator (not shown), signals with signal levels corresponding to the detected magnetic fields are obtained by causing an external comparator (not shown) outside the sensor unit 106 to convert analog signals thereinto.

In the following description, there will be mainly used, as an example, the case where the ring-shaped magnet according to the present embodiment includes N-pole magnets and S-pole magnets alternately arranged in the circumferential direction thereof as shown in A of FIG. 4, and where the sensor unit 106 according to the present embodiment outputs, as signals with signal levels corresponding to the detected magnetic fields, signals with signal levels each corresponding to either of the magnetic poles. Note that, even when the ring-shaped magnet according to the present embodiment has another configuration to be described later, the sensor unit 106 can output, as two-phase signals, signals with signal levels based on signals depending on the detected magnetic fields, similarly to the following example.

Figure 5:
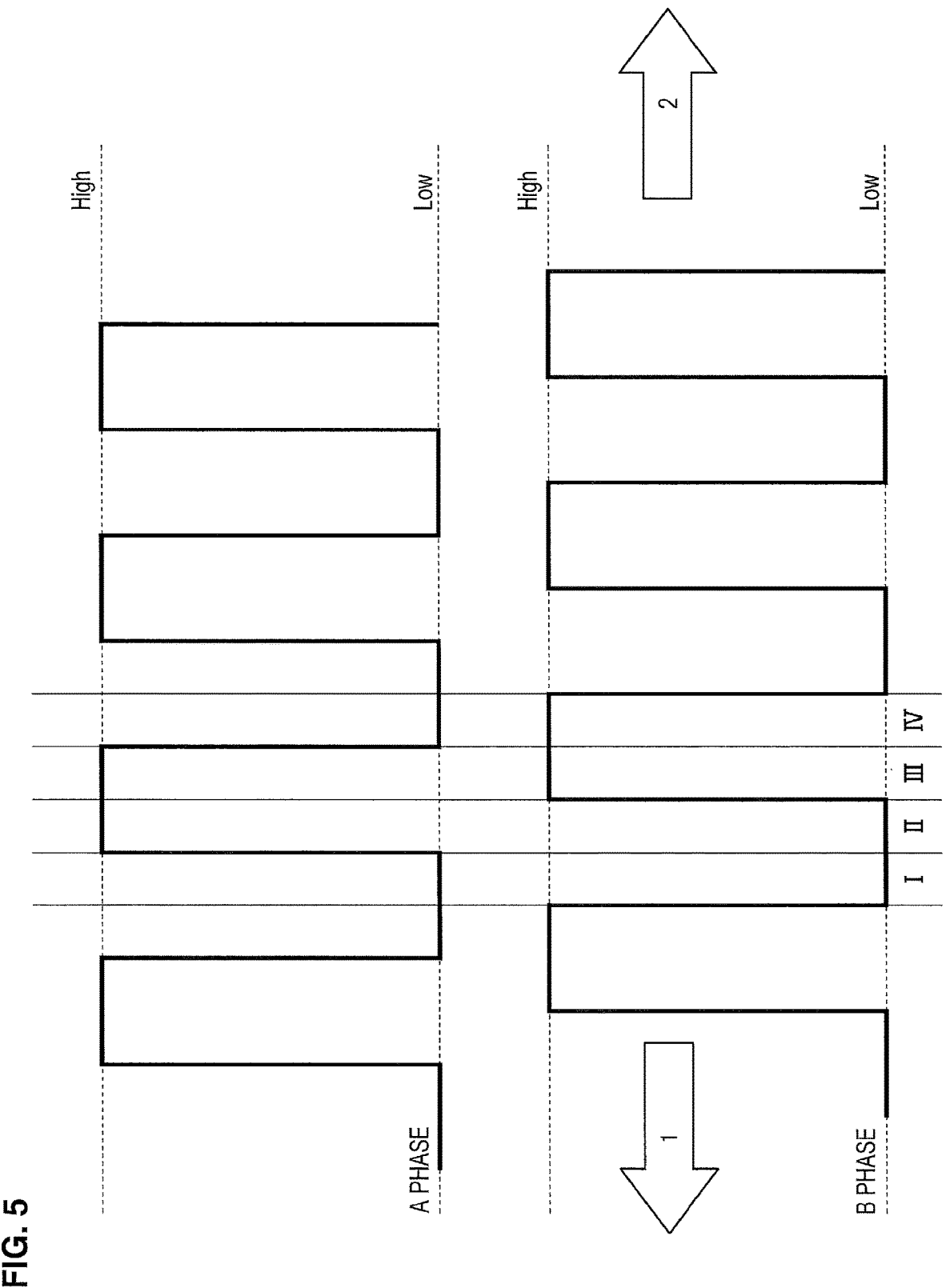
FIG. 5 is an illustration for illustrating an example of two-phase signals outputted by a sensor unit included in the operating apparatus according to the embodiment.
Figure 6:
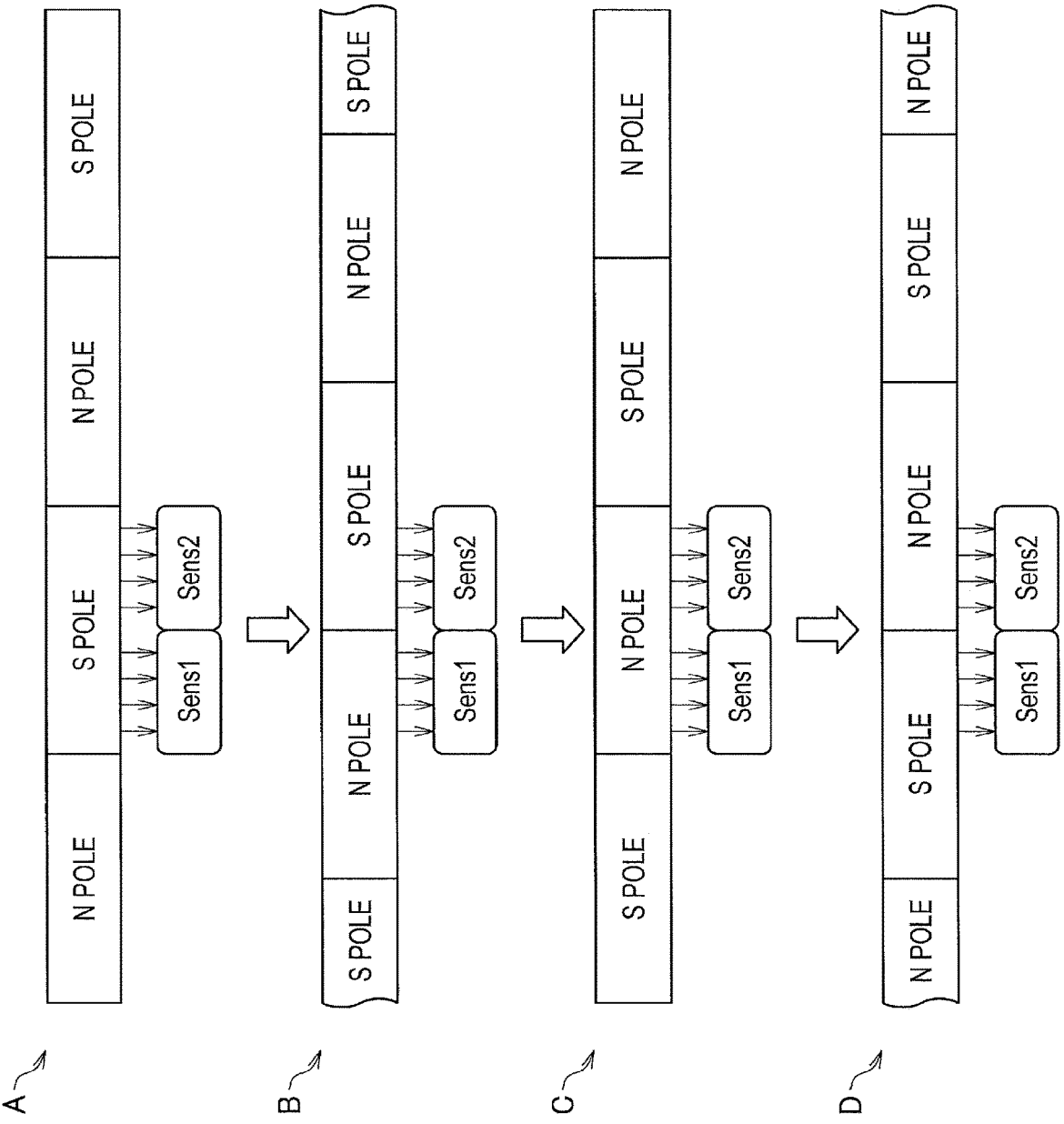
FIG. 6 is an illustration for illustrating an example of two-phase signals outputted by the sensor unit included in the operating apparatus according to the embodiment.

FIGS. 5 and 6 are illustrations for illustrating an example of two-phase signals outputted by the sensor unit 106 included in the operating apparatus 100 according to the present embodiment. FIG. 5 shows an example of A-phase and B-phase signals (two-phase signals) outputted by the sensor unit 106. FIG. 6 shows an example of positional relations between the ring-shaped magnet 104 and the sensor unit 106 respectively corresponding to "I," "II," "III" and "IV" in FIG. 5.

The sensor unit 106 outputs two-phase signals mutually shifted by 90° as shown, for example, in FIG. 5. Obviously, the phase difference between an A-phase signal and a B-phase signal is not limited to 90°.

The two sensors included in the sensor unit 106 are arranged so as to detect, at a time, the magnetic field of one polarity as shown, for example, in A and C of FIG. 6, as well as to detect, at a time, the magnetic fields of different polarities as shown, for example, in B and D of FIG. 6.

Figure 7:
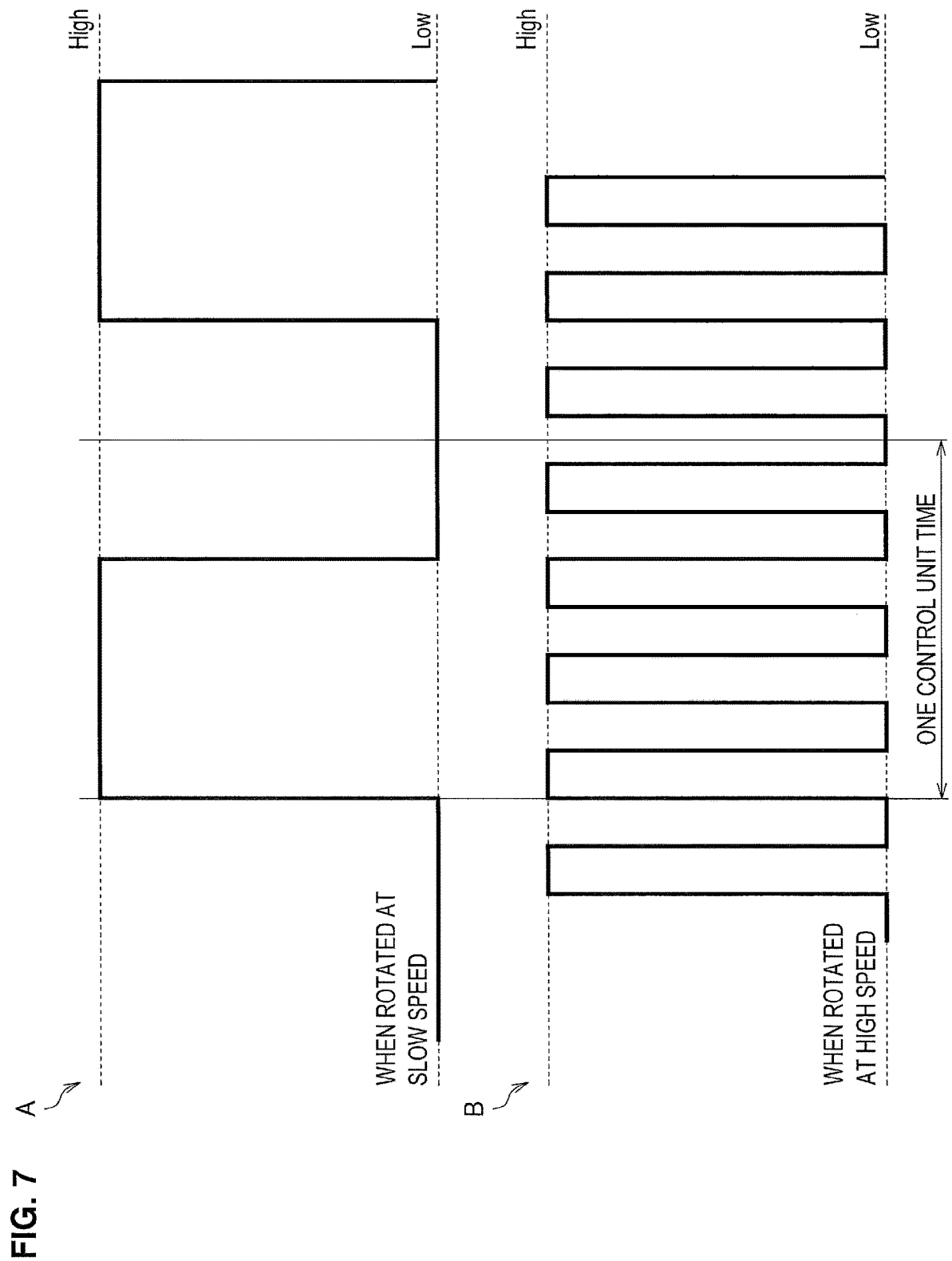
FIG. 7 is an illustration for illustrating another example of two-phase signals outputted by the sensor unit included in the operating apparatus according to the embodiment.

FIG. 7 is an illustration for illustrating another example of two-phase signals outputted by the sensor unit 106 included in the operating apparatus 100 according to the present embodiment. Each of the signal shown in A of FIG. 7 and the signal shown in B of FIG. 7 is an example of one signal (A-phase or B-phase signal) of the two-phase signals.

The sensor unit 106 latches analog signals depending on the magnetic fields detected by the sensors included therein, and outputs signals with signal levels each corresponding to the detected magnetic pole, for example. Accordingly, the sensor unit 106 outputs signals each having a waveform corresponding to the frequency of magnetic polar changes depending on rotating operation. For example, as shown in A and B of FIG. 7, the frequency of signal level changes (A of FIG. 7) of a signal outputted by the sensor unit 106 when the user rotates the operating ring 102 at slow speed is lower than the frequency of signal level changes (B of FIG. 7) outputted when the user rotates the operating ring 102 at high speed.

The sensor unit 106 outputs two-phase signals having different phases, as shown, for example, in FIG. 5, and each of these two-phase signals has a waveform depending on rotating operation by a user, as shown in FIG. 7. The processing according to user operation is realized by causing the sensor unit 106 to output two-phase signals as, for example, described above, and then by causing the processing unit (described later) or the external processing apparatus to process these two-phase signals. An example of the processing performed by the processing unit (described later) or the external processing apparatus will be described later.

Further description will be given of the exemplary configuration related to two-phase signal output in the operating apparatus 100 with reference to FIG. 4, again. The operating apparatus 100 may include a partition 108 which separates the ring-shaped magnet 104 from the sensor unit 106 as shown in B of FIG. 4, for example. The partition 108 is formed of any material, such, for example, as titanium, that does not shield magnetic fields generated by the ring-shaped magnet 104. The partition 108 may be an exterior part of the operating apparatus 100.

As described above, the sensor unit 106 includes sensors, such, for example, as hall sensors, each capable of detecting magnetic fields generated by the ring-shaped magnet 104 without contacting the ring-shaped magnet 104. Accordingly, even when the operating apparatus 100 includes the partition 108, the sensor unit 106 is still capable of outputting two-phase signals depending on the detected magnetic poles. Needless to say, when the operating apparatus 100 does not include the partition 108, the sensor unit 106 is capable of outputting two-phase signals depending on the detected magnetic poles, too.

When the operating apparatus 100 includes the partition 108, the ring-shaped magnet 104 and the sensor unit 106 are separated in different areas. Accordingly, causing the operating apparatus 100 to include the partition 108 makes it possible to place the components such as the sensor unit 106 and the lens unit to be described later in an airtight and waterproof sealed structure. Thus, including the partition 108 enables the operating apparatus 100 to have a configuration capable of preventing the components such as the sensor unit 106 and the lens unit to be described later from being damaged even when the operating apparatus 100 is sterilized by autoclaving. In other words, including the partition 108 can make the operating apparatus 100 resistant to autoclaving, for example.

The operating apparatus 100 outputs two-phase signals having different phases by using the configuration shown, for example, in FIG. 4.

Note that the configuration capable of outputting two-phase signals according to the present embodiment is not limited to that shown in FIG. 4.

For example, when applied to an apparatus that does not have to be resistant to autoclaving, the operating apparatus 100 can have a configuration not including the partition 108.

The operating apparatus 100 may include a ring-shaped magnet having a configuration different from the configuration (including N-pole magnets and S-pole magnets alternately arranged in the circumferential direction) shown in A of FIG. 4.

Figure 8:
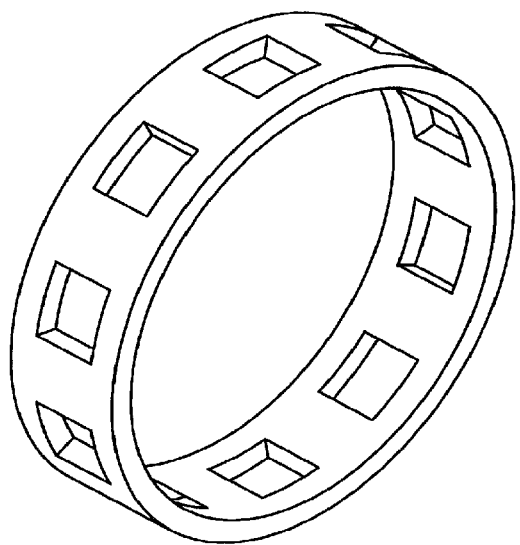
FIG. 8 is an illustration of another exemplary configuration related to two-phase signal output in the operating apparatus according to the embodiment.
Figure 8:
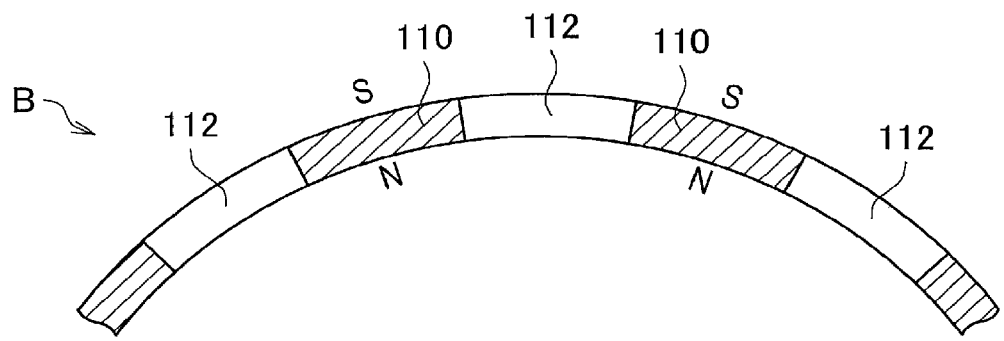

FIG. 8 is an illustration of another exemplary configuration related to two-phase signal output in the operating apparatus 100 according to the present embodiment. The part A of FIG. 8 shows another example of a ring-shaped magnet included in the operating ring 102 in the operating apparatus 100 shown, for example, in FIG. 1. The part B of FIG. 8 schematically and partially shows a cross section of the ring-shaped magnet shown in A of FIG. 8.

The ring-shaped magnet shown in FIG. 8 includes magnetized portions 110 and voids 112 alternately arranged in the ring circumferential direction. The voids 112 are formed as holes created in a member constituting the ring-shaped magnet, for example.

As shown in B of FIG. 8, each of the magnetized portions 110 is magnetically polarized so that N and S poles can be arranged in a ring radial direction. Note that, though B of FIG. 8 shows an example in which the outer side of the magnetized portion 110 is S pole and the inner side thereof is N pole, the magnetized portion according to the present embodiment is not limited thereto. For example, the outer side of the magnetized portion according to the present embodiment may be N pole while the inner side thereof being S pole.

When the ring-shaped magnet has the configuration (including the magnetized portions 110 and the voids 112 alternately arranged in the ring circumferential direction) shown in FIG. 8, the sensor unit 106 detects the magnetic fields and outputs signals depending on the detected magnetic fields. Specifically, as described above, the sensor unit 106 outputs two-phase signals by outputting signals having different phases.

Figure 9:
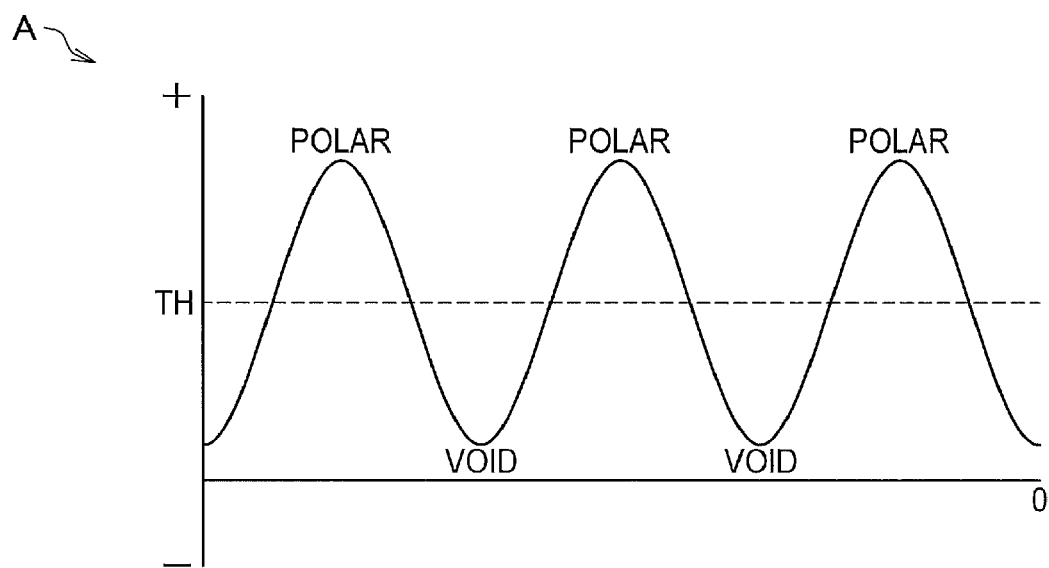
FIG. 9 is an illustration for illustrating an example of a signal outputted by the sensor unit included in the operating apparatus according to the embodiment.
Figure 9:
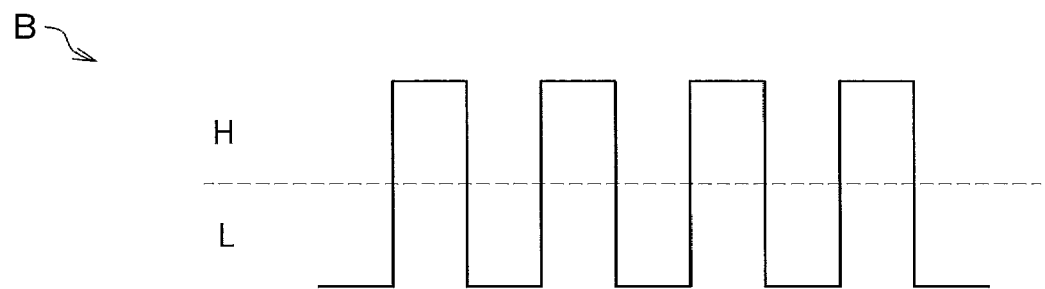

FIG. 9 is an illustration for illustrating an example of a signal outputted by the sensor unit 106 included in the operating apparatus 100 according to the present embodiment. FIG. 9 shows an example of a signal outputted by the sensor unit 106 when the ring-shaped magnet has the configuration shown in FIG. 8. Specifically, FIG. 9 exemplarily shows one-phase signal of the two-phase signals outputted by the sensor unit 106.

By causing the sensor unit 106 to detect magnetic fields, there can be obtained signals (analog signals) each having a waveform as shown, for example, in A of FIG. 9 depending on whether the magnetized portion 110 or the void 112 is in a detection area. In the example shown in FIG. 9, "POLAR" in FIG. 9 represents that the magnetized portion 110 is in the detection area at that time while "VOID" in FIG. 9 represents that the void 112 is in the detection area at that time.

By using, for example, the comparator (not shown) having a set threshold TH, the sensor unit 106 coverts the analog signals depending on the detected magnetic fields into signals each switching between high level and low level, that is, signals (digital signals) with signal levels each corresponding to the detected magnetic field, as shown, for example, in B of FIG. 9. Then, the sensor unit 106 outputs the signals with the signal levels corresponding to the detected magnetic fields.

Note that, as described above, the configuration of the sensor unit 106 according to the present embodiment is not limited to a configuration including a comparator (not shown) or the like. For example, the sensor unit 106 according to the present embodiment may have a configuration not including a comparator (not shown) or the like to output analog signals as shown, for example, in A of FIG. 9.

Even when the operating apparatus 100 according to the present embodiment includes the ring-shaped magnet shown in FIG. 8 (ring-shaped magnet including the magnetized portions 110 and the voids 112 alternately arranged in the ring circumferential direction), as described above, the operating apparatus 100 can output two-phase signals having different phases similarly to when including the ring-shaped magnet shown in FIG. 4 (ring-shaped magnet including N-pole magnets and S-pole magnets alternately arranged in the circumferential direction). In other words, the operating apparatus 100 according to the present embodiment can include either of the ring-shaped magnet magnetically polarized in the ring circumferential direction (ring-shaped magnet shown in FIG. 4) and the ring-shaped magnet magnetically polarized in the ring radial direction (ring-shaped magnet shown in FIG. 8), for example.

[2] Two-Phase Signal Based Processing According to the Present Embodiment

Next, description will be given of an example of two-phase signal based processing according to the present embodiment. In the following description, there will be used, as an example, the case where the processing unit (not shown) included in the operating apparatus 100 performs the two-phase signal based processing according to the present embodiment. Note that, even when the external processing apparatus performs the two-phase signal based processing according to the present embodiment, the external processing apparatus performs processing similar to the below-described processing performed by the processing unit (not shown).

Additionally, in the following description, there will be used, as an example, the case where the ring-shaped magnet according to the present embodiment includes N-pole magnets and S-pole magnets alternately arranged in the circumferential direction as shown in A of FIG. 4, and where, as signals with signal levels corresponding to detected magnetic fields, the sensor unit 106 outputs signals with signal levels each corresponding to either of the magnetic poles.

The processing unit according to the present embodiment performs processing based on the two-phase signals outputted by the sensor unit 106. When the two-phase signals outputted by the sensor unit 106 are signals (digital signals) with signal levels each corresponding to either of the magnetic poles as shown, for example, in FIG. 5, the processing unit according to the present embodiment performs the processing by using the two-phase signals outputted by the sensor unit 106 without any change. On the other hand, when the two-phase signals outputted by the sensor unit 106 are signals (analog signals) depending on detected magnetic fields outputted, for example, by hall sensors or the like, these signals depending on the magnetic fields are converted into signals with signal levels each corresponding to either of the magnetic poles by, for example, a comparator, and the processing unit according to the present embodiment processes the converted signals based on the signals depending on the magnetic fields.

The processing unit according to the present embodiment is realized by a processor including an operation circuit, such, for example, as a micro processing unit (MPU). The processing unit according to the present embodiment may also include various circuits such as a comparator and a latch circuit.

[2-1] First Example of Processing Performed by the Processing Unit According to the Present Embodiment The processing unit according to the present embodiment specifies rotational direction on the basis of which of the A-phase signal (one signal of the two-phase signals) and the B-phase signal (the other signal of the two-phase signals) changes in signal level earlier.

In the following description, the two-phase signals shown in FIG. 5 will be used as an example. For example, when, from the state "I" or "III" in FIG. 5, the A-phase signal changes in signal level from Low level to High level or High level to Low level earlier than the B-phase signal, the processing unit according to the present embodiment specifies that the rotational direction is the direction indicated by "1" in FIG. 5. Meanwhile, when, from the state "I" or "III" in FIG. 5, the B-phase signal changes in signal level from Low level to High level or High level to Low level earlier than the A-phase signal, the processing unit according to the present embodiment specifies that the rotational direction is the direction indicated by "2" in FIG. 5, for example. Note that the state "I" or "III" in FIG. 5 is set as a starting point in the above example, but even when the state "II" or "IV" in FIG. 5 is set as a starting point, the processing unit according to the present embodiment can specify the rotational direction on the basis of which of the two-phase signals changes in signal level earlier.

Then, the processing unit according to the present embodiment performs processing corresponding to the specified rotational direction. For example, the processing unit according to the present embodiment refers to a table (or database) or the like in which "rotational directions" correspond to "contents and parameters of processing to be performed," and performs processing corresponding to the specified rotational direction with parameters corresponding to the specified rotational direction.

For example, when specifying that the rotational direction is the direction indicated by "1" in FIG. 5, the processing unit according to the present embodiment performs zoom-in processing. On the other hand, when specifying that the rotational direction is the direction indicated by "2" in FIG. 5, the processing unit according to the present embodiment performs zoom-out processing. When performing zoom-in or zoom-out processing, the processing unit according to the present embodiment transmits control signals to, for example, an actuator to control a lens for imaging, thereby controlling operations of the actuator.

Alternatively, for example, when specifying that the rotational direction is the direction indicated by "1" in FIG. 5, the processing unit according to the present embodiment performs processing for reverse reproduction of images (processing to reproduce images in the direction to turn back time). On the other hand, when specifying that the rotational direction is the direction indicated by "2" in FIG. 5, the processing unit according to the present embodiment performs processing for forward reproduction of images (processing to reproduce images in the direction to put time forward).

The processing unit according to the present embodiment for performing the processing according to the first example performs the two-phase signal based processing according to user operation either by controlling operations of an external device outside the processing unit according to the present embodiment or by performing the processing for itself. Obviously, examples of the processing according to the first example are not limited to zoom-related processing and image reproduction related processing.

Examples of the processing corresponding to the specified rotational direction include preset processing.

However, the processing corresponding to the specified rotational direction is not limited to this. For example, the processing corresponding to the specified rotational direction may be set based on processing selection operation by a user. For example, when a user performs processing selection operation using either an operating unit (described later) operable by a user for processing selection operation and included in the operating apparatus 100 or an external operating apparatus, such as a remote controller, outside the operating apparatus 100, the processing unit according to the present embodiment sets the selected processing in the table or the like based on operation signals depending on this user operation.

In other words, as the processing corresponding to the specified rotational direction, the processing unit according to the present embodiment can perform either preset processing or processing set based on processing selection operation by a user. When, as the processing corresponding to the specified rotational direction, the processing unit according to the present embodiment performs processing based on operation signals depending on processing selection operation by a user, the user can cause the processing unit according to the present embodiment or the like to perform processing tasks respectively corresponding to multiple functions only by using a single rotationally-operable operation device, such, for example, as the operating ring 102.

[2-2] Second Example of Processing Performed by the Processing Unit According to the Present Embodiment The processing unit according to the present embodiment specifies the frequency of signal level changes of the A-phase signal (one signal of the two-phase signals) or the frequency of signal level changes of the B-phase signal (the other signal of the two-phase signals) per predetermined unit time. The predetermined unit time may be either a preset fixed time or a variable time settable based on user operation or the like.

Then, the processing unit according to the present embodiment performs processing at a processing speed corresponding to the specified frequency of signal level changes. For example, the processing unit according to the present embodiment refers to a table (or database) or the like in which "frequencies of signal level changes" correspond to "parameters of processing to be performed," and performs the set processing using the parameters corresponding to the specified frequency of signal level changes.

Examples of the processing performed by the processing unit according to the present embodiment include preset processing and processing set based on processing selection operation by a user. For example, when a user performs processing selection operation using either an operating unit (described later) operable by a user for processing selection operation and included in the operating apparatus 100 or an external operating apparatus, such as a remote controller, outside the operating apparatus 100, the processing unit according to the present embodiment sets the selected processing based on operation signals depending on this user operation. When the processing unit according to the present embodiment sets and performs processing based on operation signals depending on processing selection operation by a user, the user can cause the processing unit according to the present embodiment or the like to perform processing tasks respectively corresponding to multiple functions only by using a single rotationally-operable operation device, such, for example, as the operating ring 102.

Similarly to performing the processing according to the first example, the processing unit according to the present embodiment for performing the processing according to the second example performs the two-phase signal based processing according to user operation either by controlling operations of an external device outside the processing unit according to the present embodiment or by performing the processing for itself, for example.

In the following description, the signals shown in FIG. 7 will be used as an example. The processing unit according to the present embodiment performs processing at different speeds depending on whether the frequency of signal level changes is lower as shown in A of FIG. 7 or higher as shown in B of FIG. 7. In the following description, there will be used, as an example, the case where the set processing is focus processing. When the frequency of signal level changes is lower as shown in A of FIG. 7, focus adjustment speed is made slower than when the frequency of signal level changes is higher as shown in B of FIG. 7. On the other hand, when the frequency of signal level changes is higher as shown in B of FIG. 7, focus adjustment speed is made faster than when the frequency of signal level changes is lower as shown in A of FIG. 7.

Accordingly, when an image is so much out of focus, the user greatly moves the focused point by rotating the operating ring 102 at high speed, and thus can perform focus adjustment in a shorter time. In order to finely adjust focus, the user moves the focused point little by little by rotating the operating ring 102 at slow speed, and thus can precisely bring a desirable point into focus.

Accordingly, when performing the processing according to the second example, the processing unit according to the present embodiment performs processing at a variable speed depending on the speed of rotating operation by a user, thus providing the user with operation feeling of enhanced operability by enabling both speedy and precise controls, which are often conflicting.

[2-3] Third Example of Processing Performed by the Processing Unit According to the Present Embodiment The processing unit according to the present embodiment can perform processing that combines the processing according to the first example and the processing according to the second example.

[2-4] Fourth Example of Processing Performed by the Processing Unit According to the Present Embodiment In addition to performing processing according to any of the first to third examples, the processing unit according to the present embodiment may inform the user of information on currently performed processing.

The processing unit according to the present embodiment visually informs the user of information on a processing state (example of information on currently performed processing to be informed of) such, for example, as a zoom factor and a focus area by using any user interface including letters, indicators and/or the like. Alternatively, the processing unit according to the present embodiment may aurally inform the user of information on a processing state (example of information on currently performed processing to be informed of) such, for example, as a zoom factor by causing an audio output device such as a speaker to output sound (including music). Still alternatively, the processing unit according to the present embodiment can visually and aurally inform the user of the information on currently performed processing.

Note that examples of information on currently performed processing according to the present embodiment are not limited to those described above. Note also that the methods for informing a user of information on currently performed processing according to the present embodiment are not limited to those described above, but the processing unit according to the present embodiment can use any method capable of informing a user of information on currently performed processing.

[3] Configuration of Operating Apparatus According to the Present Embodiment Next, by using, as an example, the operating apparatus 100 shown in FIG. 1 (operating apparatus used for controlling and adjusting a medical endoscopic apparatus), description will be given of an exemplary configuration of the operating apparatus according to the present embodiment which includes the configuration related to two-phase signal output according to the present embodiment.

Figure 10:
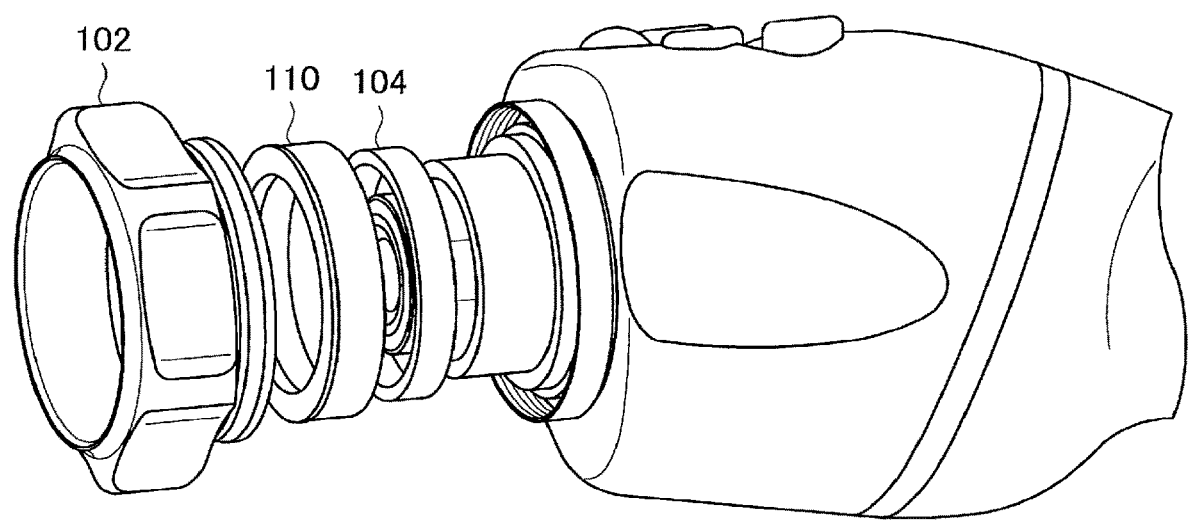
FIG. 10 is an illustration showing an exemplary configuration of the operating apparatus according to the embodiment.
Figure 11:
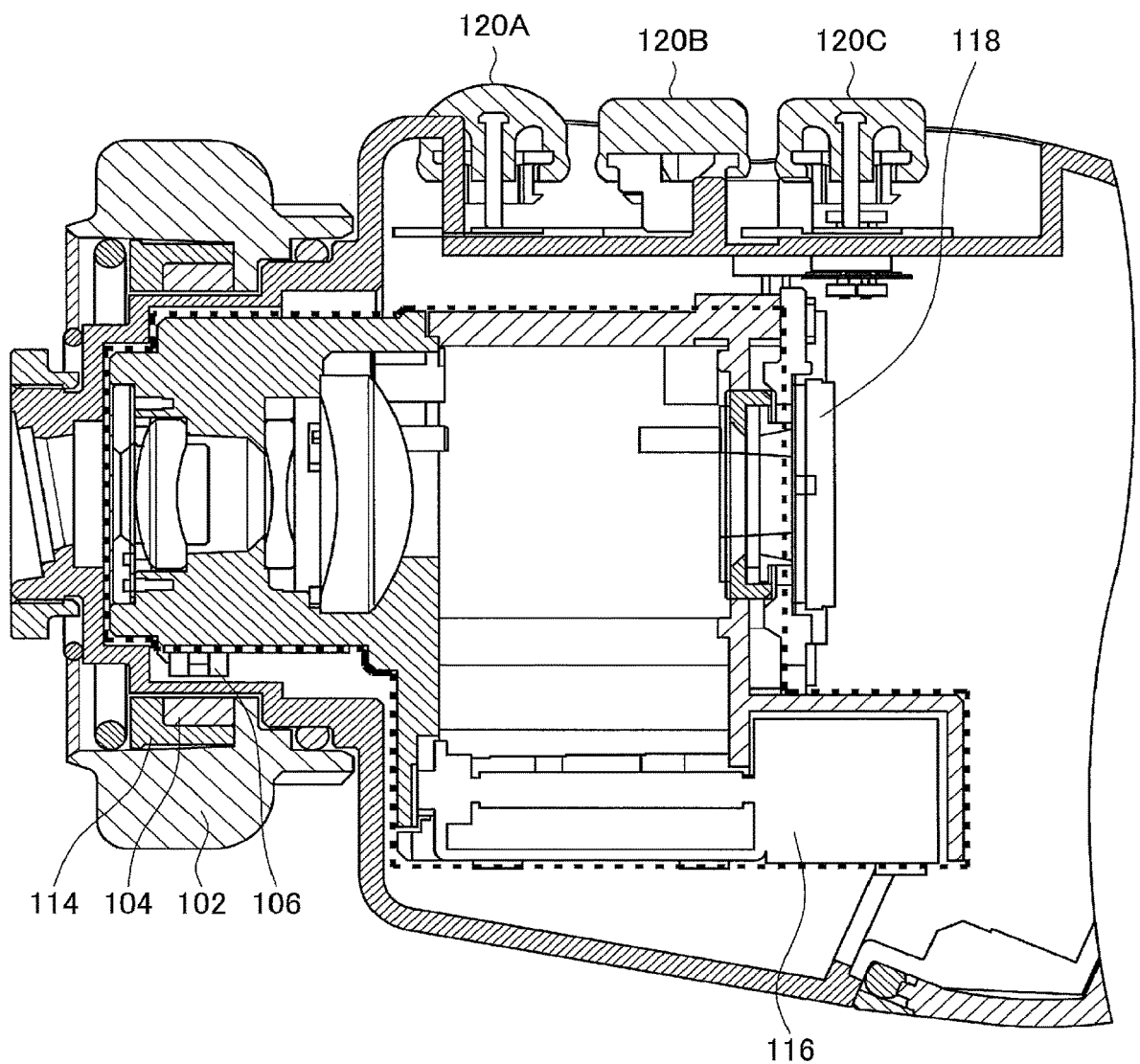
FIG. 11 is an illustration showing the exemplary configuration of the operating apparatus according to the embodiment.

FIGS. 10 and 11 are illustrations showing an exemplary configuration of the operating apparatus 100 according to the present embodiment. FIG. 10 is a partial exploded perspective view of the operating apparatus 100 shown in FIG. 1. FIG. 11 is a cross-sectional view in the vertical direction of the operating apparatus 100 shown in FIG. 1.

The operating apparatus 100 includes the operating ring 102, the ring-shaped magnet 104, the sensor unit 106, a yoke 114, a lens unit 116, an image sensor 118 and operation buttons 120A, 120B and 120C, for example. Among these, the ring-shaped magnet 104 and the sensor unit 106 are collectively equivalent to the configuration related to two-phase signal output according to the present embodiment, for example.

Additionally, the operating apparatus 100 may further include the processing unit (not shown) capable of performing the aforementioned two-phase signal based processing according to the present embodiment. In this case, the processing unit (not shown) may be included in another component such, for example, as the lens unit 116. When the operating apparatus 100 does not include the processing unit (not shown), an external processing apparatus functioning similarly to the processing unit (not shown) may perform the two-phase signal based processing according to the present embodiment, instead.

Still additionally, the operating apparatus 100 may further include a recording medium capable of storing image data, a communication device of any communication method capable of communicating with an external apparatus by radio or by cable, or the like, for example.

The operating ring 102 freely rotates clockwise or counterclockwise as described above. The operating ring 102 is coupled with the ring-shaped magnet 104, so that the ring-shaped magnet 104 rotates as the operating ring 102 rotates along with rotating operation of the operating ring 102.

The ring-shaped magnet 104 includes alternately arranged N-pole magnets and S-pole magnets, as shown, for example, in A of FIG. 4, and rotates along with rotating operation by a user.

The sensor unit 106 detects magnetic fields and outputs two-phase signals having different phases such, for example, as two signals mutually shifted by 90°. As shown, for example, in FIG. 5, the sensor unit 106 outputs, as the two-phase signals, signals with signal levels each corresponding to either of the magnetic poles on the basis of signals depending on the detected magnetic fields. Each of the two-phase signals with signal levels each corresponding to either of the magnetic poles outputted by the sensor unit 106 indicates magnetic polar changes by switching signal levels between High level and Low level.

The sensor unit 106 includes either a sensor capable of outputting two-phase signals or two sensors each capable of outputting one-phase signal, for example. The sensor unit 106 may further include a comparator, a latch circuit and the like.

The yoke 114, which is formed of a material that shields magnetic fields generated by the ring-shaped magnet 104, functions as a shield to prevent magnetic force of the ring-shaped magnet 104 from leaking outside the operating apparatus 100. Since the operating apparatus 100 includes the yoke 114, even when the operating apparatus 100 comes close to an apparatus vulnerable to magnetism, magnetic fields generated by the ring-shaped magnet 104 are prevented from affecting the apparatus.

The lens unit 116 includes a lens and an actuator to control the lens, for example. The processing unit (not shown) transmits, to the actuator, control signals based on a result of the two-phase signal based processing according to the present embodiment, for example, and the actuator is driven based on the control signals. When, for example, the processing unit (not shown) transmits, to the actuator, control signals based on a result of the two-phase signal based processing according to the present embodiment, as described above, zooming or the like depending on rotating operation by a user is enabled.

The image sensor 118 forms an image by photoelectrically converting received light. The image sensor 118 is an image sensor such as a complementary metal oxide semiconductor (CMOS) or charge coupled device (CCD) image sensor, for example.

The operation buttons 120A, 120B and 120C collectively function as an operating unit which is operable by a user for processing selection operation and the like. By, for example, performing processing selection operation using the operation buttons 120A, 120B and 120C, the user sets processing to be performed. By rotationally operating the operating ring 102, the user can control and adjust the function related to the thus set processing.

Examples of processing selection operation using the operation buttons 120A, 120B and 120C include mode switching operation for switching between the AF mode and the MF mode, and state switching operation for switching between various "processing states." Providing the operation buttons 120A, 120B and 120C in the vicinity of the operating ring 102 (for example, a position allowing the user to operate the operation buttons 120A, 120B and 120C with the forefinger or the thumb simultaneously with operating the operating ring 102) as shown in FIG. 11 enables the user to perform, with one hand, both the rotating operation using the operating ring 102 and the operation using the operation buttons 120A, 120B and 120C. For example, by using the operating ring 102 and the operation buttons 120A, 120B and 120C, the user can perform, with one hand, both the mode switching operation and the operation of the operating ring 102.

As described above, by performing processing selection operation using, for example, the operation buttons 120A, 120B and 120C, the user can select which processing to set as to be performed depending on the user's rotating operation of the operating ring 102. This enables the operating apparatus 100 to switch between processing tasks that are performable by the user's rotating operation of the operating ring 102. In other words, the user can control and adjust multiple functions by using the operating ring 102.

Accordingly, using the operating apparatus 100 can realize, for example, the following action, and thus the operating apparatus 100 can improve user convenience.

By performing processing selection operation to switch from "processing related to an imaging function (processing related to zooming, focusing and the like, for example)" to "processing related to an imaged image reproduction function (processing related to selection, starting reproduction, rewinding, fast-forwarding and the like of imaged images, for example), a surgeon (example of a user) during surgery can check imaged images without swapping the operating apparatus 100 for another operating apparatus related to image reproduction.

Moreover, since multiple functions can be controlled and adjusted by using the operating ring 102, the number of operation devices for controlling and adjusting functions can be reduced, and thus the operating apparatus according to the present embodiment can be miniaturized.

The operating apparatus 100 includes the configuration related to two-phase signal output (the ring-shaped magnet 104 and the sensor unit 106) according to the present embodiment, as shown, for example, in FIG. 11. On that basis, the processing depending on rotating operation by a user is performed based on the two-phase signals according to the present embodiment as in the aforementioned two-phase signal based processing according to the present embodiment. Accordingly, with the configuration shown, for example, in FIG. 11, the operating apparatus 100 can cause processing according to user operation to be performed.

Moreover, in response to the user's processing selection operation using, for example, the operation buttons 120A, 120B and 120C, the operating apparatus 100 can switch between processing tasks that are performable by the user's rotating operation using the operating ring 102. This enables the user to control and adjust multiple functions by using the operating ring 102. Thus, the operating apparatus 100 can improve user convenience and can be miniaturized.

Moreover, by causing the processing unit (not shown) to perform the processing according to the second example shown in the above [2-2], the operating apparatus 100 provides the user with operation feeling of enhanced operability by enabling both speedy and precise controls, which are often conflicting.

Note that the configuration of the operating apparatus according to the present embodiment is not limited to that shown in FIGS. 10 and 11.

For example, the operating apparatus according to the present embodiment does not have to include any components, such as the lens unit 116, the image sensor 118 and the operation buttons 120A, 120B and 120C, other than the configuration related to two-phase signal output (the ring-shaped magnet 104 and the sensor unit 106) according to the present embodiment. These components other than the configuration related to two-phase signal output according to the present embodiment may be included in an external apparatus outside the operating apparatus. Moreover, the operating apparatus according to the present embodiment can have a configuration not including the operating ring 102 or the yoke 114.

Furthermore, the operating apparatus according to the present embodiment does not have to include the processing unit (not shown), and an external processing apparatus functioning similarly to the processing unit (not shown) may perform the two-phase signal based processing according to the present embodiment, instead. In this case, an operation system including both the operating apparatus according to the present embodiment having the configuration related to two-phase signal output according to the present embodiment and the external processing apparatus to perform the two-phase signal based processing according to the present embodiment provides effects similar to the aforementioned effects provided by the operating apparatus 100.

The operating apparatus according to the present embodiment may further include a member (such as a member for adjusting rotatability, for example) for providing predetermined operation feeling to the user who is performing rotating operation using the operating ring 102. The operating apparatus according to the present embodiment, in which the sensor unit 106 is placed so as not to contact the ring-shaped magnet 104, can be further provided with the member for providing predetermined operation feeling.

Program According to the Present Embodiment

When a processor or the like in a computer executes a program (program that enables the performing of the two-phase signal based processing according to the present embodiment such as the processing according to any of the first to fourth examples respectively shown in the above [2-1] to [2-4]) for causing the computer to function as a processing unit according to the present embodiment (or a processing apparatus according to the present embodiment), the two-phase signal based processing according to the present embodiment depending on user operation can be performed.

When a processor or the like in a computer executes a program for causing the computer to function as a processing unit according to the present embodiment (or a processing apparatus according to the present embodiment), there are provided effects similar to the aforementioned effects resulting from the two-phase signal based processing according to the present embodiment.

The preferred embodiment of the present disclosure has been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

For example, the above shows that a program (computer program) causing a computer to function as a processing unit according to the present embodiment (or a processing apparatus according to the present embodiment) is provided, but the present embodiment can further provide a recording medium caused to store the program.

The above configuration shows an example of the present embodiment and naturally comes under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

An operating apparatus for a medical apparatus, the operating apparatus including:

a ring-shaped magnet magnetically polarized in a circumferential direction or a radial direction and configured to rotate along with rotating operation by a user; and a sensor unit configured to detect a magnetic field and to output a signal depending on the detected magnetic field, wherein the sensor unit outputs two-phase signals having different phases.

(2)

The operating apparatus for a medical apparatus according to (1), wherein the sensor unit outputs, as the two-phase signals, signals with signal levels each based on the signal depending on the detected magnetic field.

(3)

The operating apparatus for a medical apparatus according to (1), wherein the ring-shaped magnet includes an N-pole magnet and an S-pole magnet alternately arranged in the circumferential direction.

(4)

The operating apparatus for a medical apparatus according to (1), wherein the ring-shaped magnet includes a magnetized portion and a void alternately arranged in the circumferential direction, the magnetized portion being magnetically polarized so that an N pole and an S pole are arranged in the radial direction.

(5)

The operating apparatus for a medical apparatus according to any one of (1) to (5), wherein the sensor unit is placed so as not to contact the ring-shaped magnet, and is immovable by magnetic force of the ring-shaped magnet.

(6)

The operating apparatus for a medical apparatus according to any one of (1), to (5) the operating apparatus further including:

a partition which separates the ring-shaped magnet from the sensor unit but which does not shield a magnetic field.

(7)

The operating apparatus for a medical apparatus according to any one of (1) to (6), wherein the sensor unit includes a sensor configured to output the two-phase signals.

(8)

The operating apparatus for a medical apparatus according to any one of (1) to (6), wherein the sensor unit includes two sensors one of which detects one signal of the two-phase signals, and the other of which detects the other signal of the two-phase signals.

(9)

The operating apparatus for a medical apparatus according to (8), wherein the ring-shaped magnet includes an N-pole magnet and an S-pole magnet alternately arranged in the circumferential direction, and wherein the two sensors included in the sensor unit detect, at a time, either a magnetic field of one polarity or magnetic fields of different polarities.

(10)

The operating apparatus for a medical apparatus according to any one of (1) to (9), wherein the sensor unit outputs the two-phase signals mutually shifted by 90°.

(11)

The operating apparatus for a medical apparatus according to any one of (1) to (10), the operating apparatus further including:

a processing unit configured to perform processing based on the two-phase signals, wherein, when each of the two-phase signals is the signal depending on the detected magnetic field, the processing unit performs processing on a signal with a signal level based on the signals depending on the detected magnetic field.

(12)

The operating apparatus for a medical apparatus according to (11), wherein the processing unit specifies a rotational direction on the basis of which of one signal and the other signal of the two-phase signals changes in signal level earlier, and performs processing corresponding to the specified rotational direction.

(13)

The operating apparatus for a medical apparatus according to (11) or (12), wherein the processing unit specifies a frequency of signal level changes of one signal of the two-phase signals or a frequency of signal level changes of the other signal of the two-phase signals per predetermined unit time, and performs processing at a processing speed corresponding to the specified frequency of signal level changes.

(14)

The operating apparatus for a medical apparatus according to any one of (11) to (13), wherein the processing unit performs either preset processing or processing set based on processing selection operation by a user.

(15)

The operating apparatus for a medical apparatus according to (14), the operating apparatus further comprising:
an operating unit which is operable by a user for processing selection operation,
wherein the processing unit sets processing corresponding to an operation signal depending on the processing selection operation that the user performs by operating the operating unit, and performs the set processing.

(16)

The operating apparatus for a medical apparatus according to any one of (11) to (15),
wherein the processing unit informs a user of information on currently performed processing.

Reference Signs List 10, 20, 102 operating ring
100 operating apparatus
104 ring-shaped magnet
106 sensor unit
108 partition
110 magnetized portion
112 void
114 yoke
116 lens unit
118 image sensor
120A, 120B, 120C operation button

The invention claimed is:

1. An operational apparatus for a medical device, the operational apparatus comprising:
a ring-shaped magnet polarized in a predetermined direction, the ring-shaped magnet to rotate in response to manual manipulation by a user;
at least one sensor to detect a magnetic field and to output a signal based on the detected magnetic field, the at least one sensor being arranged in an airtight and waterproof shielded area, wherein the at least one sensor is entirely encircled by the ring-shaped magnet;
a partition that forms the airtight and waterproof shielded area and separates the ring-shaped magnet from the at least one sensor, but does not shield a magnetic field, wherein the partition between the ring-shaped magnet and the at least one sensor is a non-ferromagnetic material; and
an operating ring that covers the ring-shaped magnet.

2. The operational apparatus for the medical device according to claim 1, wherein the medical device is an endoscope.

3. The operational apparatus for the medical device according to claim 1, wherein the medical device is a surgical device.

4. The operational apparatus for the medical device according to claim 1, wherein the at least one sensor outputs two-phase signals having different phases.

5. The operational apparatus for the medical device according to claim 4, wherein the at least one sensor outputs signals with each respective signal level based on the detected magnetic field, as the two-phase signals.

6. The operational apparatus for the medical device according to claim 1, wherein the ring-shaped magnet includes an N-pole magnet and an S-pole magnet alternately arranged in a circumferential direction.

7. The operational apparatus for the medical device according to claim 1, wherein the ring-shaped magnet includes a magnetized portion and a void alternately arranged in a circumferential direction, the magnetized portion being magnetically polarized so that an N pole and an S pole are arranged in a radial direction.

8. The operational apparatus for the medical device according to claim 1, wherein the at least one sensor is placed so as not to contact the ring-shaped magnet, and is immovable by magnetic force of the ring-shaped magnet.

9. The operational apparatus for the medical device according to claim 4, wherein the at least one sensor outputs the two-phase signals.

10. The operational apparatus for the medical device according to claim 4, wherein the at least one sensor includes two sensors a first one of which detects a first one signal of the two-phase signals, and a second one of which detects a second one signal of the two-phase signals.

11. The operational apparatus for the medical device according to claim 10, wherein the ring-shaped magnet includes an N-pole magnet and an S-pole magnet alternately arranged in a circumferential direction, and
wherein the two sensors included in the at least one sensor detect either a magnetic field of one polarity or magnetic fields of different polarities.

12. The operational apparatus for the medical device according to claim 4, wherein the at least one sensor outputs the two-phase signals mutually shifted by 90°.

13. The operational apparatus for the medical device according to claim 4, further comprising:
processing circuitry configured to perform processing based on the two-phase signals,
wherein, when each of the two-phase signals is the signal based on the detected magnetic field, the processing circuitry performs processing on a signal with a signal level based on the detected magnetic field.

14. The operational apparatus for the medical device according to claim 13, wherein the processing circuitry specifies a rotational direction on the basis of which signal of the two-phase signals changes signal level earlier, and performs processing corresponding to the specified rotational direction.

15. The operating apparatus for a medical apparatus according to claim 13, wherein the processing circuitry specifies a frequency of signal level changes of a first signal of the two-phase signals or a frequency of signal level changes of a second signal of the two-phase signals per predetermined unit time, and performs processing at a processing speed corresponding to the specified frequency of signal level changes.

16. The operational apparatus for the medical device according to claim 13, wherein the processing circuitry performs either preset processing or processing set based on processing selection operation by a user.

17. The operational apparatus for the medical device according to claim 16, further comprising:
an operational device which is operable by a user to perform a processing selection operation,
wherein the processing circuitry sets processing corresponding to an operation signal based on the processing selection operation, and performs the set processing.

18. The operational apparatus for the medical device according to claim 13, wherein the processing circuitry transmits information on currently performed processing for display.

19. The operational apparatus for the medical device according to claim 1, wherein the predetermined direction is a circumferential direction or a radial direction.

20. The operational apparatus for the medical device according to claim 1, wherein selection, starting of reproduction, rewinding, fast-forwarding, zooming and/or focusing is controlled by circuitry based on the signal of the at least one sensor.

21. The operational apparatus for the medical device according to claim 1, wherein the at least one sensor is arranged in an area completely encircled by the ring-shaped magnet.

22. The operational apparatus for the medical device according to claim 1, wherein the manual manipulation by the user corresponds to a rotation operation by the user.

23. The operational apparatus for the medical device according to claim 22, wherein rotating speed, rotation direction and/or amount of rotation is detected by circuitry based on the signal of the at least one sensor.

* * * * *